United States Patent [19]

Kurahashi et al.

[11] Patent Number: 4,504,581

[45] Date of Patent: Mar. 12, 1985

[54] METHOD FOR PRODUCING L-HISTIDINE BY FERMENTATION

[75] Inventors: Osamu Kurahashi, Kawasaki; Takayasu Tsuchida, Yokohama; Hiroki Kawashima, Kawasaki; Hitoshi Enei, Zushi; Shigeru Nakamori, Yokohama, all of Japan

[73] Assignee: Ajinomoto Company Incorporated, Tokyo, Japan

[21] Appl. No.: 448,792

[22] Filed: Dec. 10, 1982

[30] Foreign Application Priority Data

Dec. 18, 1981 [JP] Japan ............................. 56-204577

[51] Int. Cl.³ .................. C12P 13/24; C12N 15/00; C12R 1/125
[52] U.S. Cl. .................. 435/107; 435/172.3; 435/839
[58] Field of Search .............. 435/107, 172.1, 172.3

[56] References Cited

U.S. PATENT DOCUMENTS 3,902,966 9/1975 Chibata et al. .............. 435/107
4,388,405 6/1983 Sano et al. .............. 435/107

*Primary Examiner*—Lionel M. Shapiro
*Attorney, Agent, or Firm*—Oblon, Fisher, Spivak, McClelland & Maier

[57] ABSTRACT

L-Histidine producing microorganisms which have been constructed by introducing a recombinant plasmid DNA inserted on a chromosomal DNA fragment into a recipient strain of the genus Bacillus. These microorganisms are employed to produce L-histidine in higher than normal yields. The recombinant plasmid DNA inserted is obtained from a donor mutant strain of *Bacillus subtilis* which is resistant to certain L-histidine antagonists. The resistant plasmid confers the properties of the mutant strain upon the recipient *Bacillus subtilis* to make its high yield of product even higher.

14 Claims, No Drawings

METHOD FOR PRODUCING L-HISTIDINE BY FERMENTATION

BACKGROUND OF THE INVENTION

1. Field of the Invention

The present invention relates to a method for producing L-histidine by fermentation, and particularly to a method for producing L-histidine with a microorganism of the genus Bacillus constructed by a gene splicing technique.

2. Description of the Prior Art

In the past, in order to render a wild strain capable of producing L-histidine from carbohydrates, it has been necessary to induce artificial mutants from the wild strain. In this regard, there are many known L-histidine producing artificial mutants.

Examples of known histidine producing microorganisms include mutants of Brevibacterium and Corynebacterium resistant to 2-thiazolealanine (U.P. Pat. No. 3,716,453), mutant of Corynebacterium resistant to histidine-analog and purine-analog (Japanese Published Examined patent application No. 18798/1977), mutants of Serratia (U.S. Pat. No. 3,902,966), mutants of Proteus (Japanese Published Unexamined patent application No. 92588/1972), mutants of Brevibacterium resistant to 2-thiazolealanine and sulfa-drug (Japanese Published Examined patent application No. 23594/1976).

Another approach to increase the productivity of histidine in microorganisms is suggested in Japanese Published Unexamined patent application No. 165798/1979). In this technique, *Escherichia coli* strains transformed with a recombinant plasmid DNA and constructed by a gene splicing technique to produce L-histidine are disclosed.

However, it is requested still to produce L-histidine by fermentation in higher efficiency than the known methods.

SUMMARY OF THE INVENTION

It has now been found that the L-histidine producing microorganisms, which have been constructed by introducing a recombinant plasmid DNA inserted with a chromosomal DNA fragment controlling resistance to a histidine-antagonist obtained from a mutant of the genus Bacillus resistant to the histidine-antagonist, into a recipient strain of the genus Bacillus, produce L-histidine in higher yield than the mutant used as the DNA-donor or the recipient strain.

DETAILED DESCRIPTION OF PREFERRED EMBODIMENTS

The L-histidine producing microorganisms used in the method of the present invention are constructed by introducing a recombinant plasmid DNA inserted with a chromosonal DNA fragment controlling resistance to a histidine-antagonist obtained from a mutant of the genus Bacillus resistant to the histidine-antagonist, into a recipient strain of the genus Bacillus.

The histidine-antagonists of the present invention inhibit the growth of Bacillus, but the inhibition is suppressed partly or completely when L-histidine coexists in the medium, and examples of the histidine-antagonists are 1, 2, 4-triazolealanine, 2-thiazolealanine, α-methylhistidine and 3-amino-1, 2, 4-triazolealanine.

Although any mutants of the genus Bacillus resistant to histidine-antagonist can be used as the DNA-donors for chromosomal DNA fragment controlling resistance to the histidine-antagonist, mutants having higher resistance to the histidine-antagonist are preferred. In many cases, better results can be obtained when mutants having higher productivity of L-histidine are used as the DNA-donor. The mutant resistant to the histidine-antagonist can be obtained by a conventional manner, such as exposing parent strain to 250 μg/ml of N-methyl-N'-nitro-N-nitrosoguanidine, and isolating the strain capable of growing in a medium containing an amount of the histidine-antagonist inhibitive to the growth of the parent strain.

Extraction of chromosomal DNA can be carried out by a conventional manner as described in Bacteriol, 89, 1065, (1965).

As the vector DNA, plasmid DNAs which propagate in hosts of Bacillus are used. Typical vector DNAs are pCT 127, pC 194, pC 221, pC 223 and pUB 112 (Proc. Natl. Acad. Sci. U.S.A., 74, 1680–1682 (1977)), pUB 110 (J. Bacteriol., 134, 318–329 (1978), and pTP 4 and pTP 5 (Microbiol Letters, 5, 55–59 (1978)), all of which are derived from plasmids of Staphylococcus, and pLS 15 and pLS 28 (J. Bacteriol., 131, 699–701 (1977)), pLS 13 (J. Bacteriol., 129, 1487–1494 (1977)), and pPL, pPL 2 (J. Bacteriol 124, 484 (1975), all of which are derived from plasmids of Bacillus.

The chromosomal DNA is digested with a restriction endonuclease by a well known method (Biochem. Biophys. Acta, 383, 457, (1975)). Various kinds of restriction endonucleases can be used if the degree of digestion is controlled by changing reaction time.

The vector DNA is also cleaved with a restriction endonucleases. Suitable restriction endonuclease for each vector DNA are disclosed in the literature shown in the parentheses above.

Recombination of DNA to prepare the recombinant plasmid can be carried out by a ligation reaction with a ligase, or by incorporating with terminal transferase deoxyadenylic acid and thymidylic acid, or deoxyguanylic acid and deoxycytidylic acid, into the chromosomal DNA fragment and cleaved vector DNA, and by subjecting the modified chromosomal DNA fragment and cleaved DNA to an annealing reaction.

The recombinant DNA thus obtained can be incorporated into the DNA-recipient by treating the cell of the DNA-recipient with calcium chloride to increase the permeability as is reported regarding *E. coli* K-12 (Mandel, M. and Higa, A., J. Mol. Biol., 53, 159 (1970)), or by applying to the incorporating cells of the DNA-recipient at a specific stage of growth when cells become capable of incorporating plasmids (competent cells) as is reported for *Bacillus subtilis* (Duncan, C. H., Wilson, G. A. and Young, F. E., Gene 1, 153 (1977)). The recombinant DNA can also be incorporated into the DNA-recipient by forming protoplast or spheroplast of the DNA-recipient which easily incorporates plasmid DNA as is known for *Bacillus subtilis,* actinomycetes and yeast (Chang, S. and Cohen, S. N., Molec. Gen. Genet, 168, 111 (1979)); Bibb, M. J. Ward, J. M. and Hopwood, O. A., Nature, 274, 398 (1978); Hinnen, A., Hicks, J. B. and Fink, G. R., Proc. Natl, Acad. Sci., USA, 75, 1929 (1978)), The recipients for the recombinant DNA are microorganisms of the genus Bacillus. It is convenient to use, as the DNA recipient, microorganisms sensitive to a histidine-analogue and requiring histidine for growth for the selection of transformants having a recombinant DNA inserted with chromosomal DNA fragment controlling resistance to histidine-antagonist. When the recombinant plasmid DNA inserted with a chromosomal DNA fragment controlling resistance to a histidine-antagonist is used for transformation after selection of the recombinant plasmid DNA using a host sensitive to the histidine-antagonist and requiring L-histidine for growth, microorganisms resistant to histidine-antagonist and having no requirement of L-histidine for growth can be used as the DNA recipient.

The desired transformants are those which become resistant to histidine-antagonist and are capable of producing L-histidine in case microorganisms sensitive to histidine-antagonist and requiring L-histidine for growth are used as the recipients. In case microorganisms resistant to histidine-antagonist and having no requirement of L-histidine for growth, the desired transformants are those which have the characteristics possessed by the vector DNA as the marker for selection.

The methods of cultivation of the L-histidine producing transformants thus obtained are conventional, and are similar to the methods for the cultivation of known L-histidine producing microorganisms. The aqueous culture medium employed is a conventional one containing a carbon source, nitrogen source, inorganic ions and, when required, minor organic nutrients such as vitamine and amino acid.

As for the carbon source, a carbohydrate such as glucose, sucrose, lactose, or fructose or a raw material containing such saccharide (such as strach hydrolysate, molasses and fruit juice) is used. Gaseous ammonia, aqueous ammonia, ammonium salts and other nitrogen containing materials can be used as the nitrogen source.

Cultivation is conducted under aerobic conditions in which the pH and the temperature of the aqueous culture medium are adjusted to a suitable level previously determined and continued until production of L-histidine ceases.

EXAMPLE 1

(1) Extraction of chromosomal DNA

Bacillus subtilis AJ 11733 (FERM-BP 217) requiring L-arginine and L-leucine and resistant to 1, 2, 4-DL-triazolealanine was cultured in 1 l of "Bact Penassay Broth" (Difco) at 30° C. for 2 hours with shaking, and cells in exponential growth phase were harvested. Chromosomal DNA was extracted from the cells by a conventional phenol-method, (J. Bacteriol., 89, 1065 (1965), and 4.0 mg of purified DNA was obtained.

(2) Insertion of chromosomal DNA fragment into vector

As the vector, pUB 110 possessing genetic information of kanamycin-resistance and neomycin-resistance was used.

Ten μg of the chromosomal DNA obtained in step (1) and 5 μg of the vector DNA were digested separately with endonuclease Eco RI at 37° C. for 1 hour, and thereafter the two reaction mixture were heated at 65° C. for 10 minutes and mixed. The mixed solution was subjected to ligation reaction by a $T_4$ phage DNA-ligase in the presence of ATP and dithreitol at 10° C. for 24 hours.

(3) Genetic transformation with the plasmid having histidine producing gene

Bacillus subtilis AJ 11732 (FERM-BP 224) which requires L-arginine, L-leucine and L-histidine was cultured in "Penassay Broth" (Difco) at 30° C. overnight with shaking, and thereafter culturing at 37° C. for 4 hours with shaking in Medium-I (containing 0.5 g/dl glucose, 0.2 g/dl $(NH_4)_2SO_4$, 0.6 g/dl $KH_2PO_4$, 1.4 g/dl $K_2HPO_4$, 0.02 g/dl $MgSO_4.7H_2O$, 0.1 g/dl sodium citrate, 0.2 g/dl yeast extract, 10 mg/dl L-histidine, 25 mg/dl L-arginine and 5 mg/dl L-leucine), and further cultured, after the cultivation in Medium-I, at 37° C. for 1.5 hours with shaking in Medium-II (containing 0.5 g/dl glucose, 0.2 g/dl $(NH_4)_2SO_4$, 0.6 g/dl $KH_2PO_4$, 1.4 g/dl $K_2HPO_4$, 0.12 g/dl $MgSO_4.7H_2O$, 0.1 g/dl sodium citrate 0.02 g/dl yeast extract, 5 mg/dl L-arginine and 0.5 mg/dl L-leucine). Thus, competent cell having the ability of plasmid uptake was obtained. (C. Anagnostopoulos, J. Spizizen: J. Bacteriol., 81, 741, (1961)).

A suspension of the competent cell was added with the recombinant plasmid having histidine producing gene obtained in step (2), and incubated at 37° C. for 2 hours with shaking to complete transformation reaction.

The cell-suspension was transferred onto a minimum medium prepared by adding 5 μg/ml kanamycin, 10 mg/dl L-leucine, 10 mg/dl L-arginine, 50 mg/dl 1, 2, 4-triazolealanine and 2 g/dl agar to a basal minimum medium of pH 7.2 containing 0.6 g/dl $KH_2PO_4$, 1.4 g/dl $K_2HPO_4$, 0.2 g/dl $(NH_4)_2SO_4$, 0.1 g/dl sodium citrate, 0.02 g/dl $MgSO_4.7H_2O$, and 0.5 g/dl glucose. After 3 days cultivation at 37° C., three colonies appeared on the agar-medium.

Among the three transformants, AJ 11734 (FERM-BP 218) which had highest productivity of L-histidine was selected. DNA in AJ 11734 was extracted from it by C. I. Kado's phenol method (J. Bac., 145, 3, 1365 (1981)). Plasmid DNA and chromosomal DNA were separated by agarose-gel electrophoresis, and plasmid DNA obtained was purified by dialysis.

The purified plasmid was incorporated into AJ 11733, which produces L-histidine, by the manner shown in step (3), and as the desired transformant, kanamycin and 1, 2, 4 triazolealanine-resistant AJ 11735 (FERM-BP 219) was obtained.

(4) Histidine production by the new histidine producers

L-histidine productivity of AJ 11733, AJ 11734 and AJ 11735 was tested as follows.

Twenty ml batches of a culture medium at pH 7.0, which contained, per deciliter, 8 g glucose, 1 g $NH_4Cl$, 0.2 g KCl, 0.1 g $KH_2PO_4$, 0.04 g $MgSO_4.7H_2O$, 0.4 g "casamino acid" (Difco), 1 mg $FeSO_4.4H_2O$, 1 mg $MnSO_4.4H_2O$, 20 mg L-arginine, 20 mg L-leucine and 4 g $CaCO_3$, were placed in 500 ml-shaking flasks. Five μg/ml kanamycin was added further to the medium for AJ 11734 and AJ 11735.

Cultivation was carried out at 30° C. for 96 hours with shaking.

The amounts of L-histidine in the supernatant of the resulting culture media were determined by microbiological-assay, and are shown in Table 1.

TABLE 1

| Microorganism tested | L-Histidine accumulated (mg/dl) |
|---|---|
| AJ 11733 | 110 |
| AJ 11734 | 150 |
| AJ 11735 | 230 |

AJ 11732 can be easily obtained by removing plasmid from AJ 11734 by a conventional manner as mentioned below: AJ 11734 is cultured with shaking in 4 ml of CMG-2 medium at pH 7.0 containing 0.5 g/dl glucose, 1 g/dl yeast extract, 1 g/dl peptone and 0.5 g/dl NaCl and placed in 20 ml-test tube. The temperature is adjusted to 30° C. from initiation to 12 hours, and 41° C. from 12 hours to 36 hours. Cells in the resulting culture broth are collected, suspended in sterilized water, and spread on a CMG-2-agar-plate. The plate is then incubated at 30° C. for one day, and is replicated onto the second CMG-2-agar-plate containing 10 µg/ml kanamycin. The second CMG-2-agar-plate is incubated at 30° C. for 1 day. The strain which can not grow on the second CMG-2-agar-plate is separated as AJ 11732.

What is claimed is:

1. A method for producing L-histidine by fermentation which comprises:
    (a) aerobically culturing an L-histidine producing microorganism constructed by incorporating a recombinant plasmid DNA inserted on a DNA fragment controlling resistance to a histidine antagonist said fragment obtained form the chromosomal DNA of the mutant of the genus Bacillus which is resistant to the histidine antatonist, into a recipient strain of the genus Bacillus and
    (b) recovering the L-histidine accumulated in the culture medium.

2. The method of claim 1, wherein said mutant belongs to *Bacillus subtilis*.

3. The method of claim 1, wherein said recipient strain belongs to *Bacillus subtilis*.

4. The method of claim 1, wherein said histidine-antagonist is 1, 2, 4-triazolealanine.

5. The method of claim 1, wherein said recipient strain requires L-histidine for growth.

6. The method of claim 1, wherein said recipient strain is resistant to a histidine-antagonist.

7. A method for producing L-histidine by fermentation which comprises:
    aerobically culturing in a culture medium an L-histidine producing microorganism which is produced by incorporating a first recombinant plasmid into a first recipient strain of the genus Bacillus, said first recombinant plasmid containing a DNA fragment controlling resistance to a histidine-antagonist, obtained from a transformant of the genus Bacillus which is produced by incorporating a second hybrid plasmid into a second recipient strain of the genus Bacillus, said second recombinant plasmid containing a DNA fragment controlling resistance to a histidine-antagonist, obtained from a mutant of the genus Bacillus resistant to a histidine-antagonist, said second recipient strain of the genus Bacillus being an L-histidine requiring strain, and said first recipient strain of the genus Bacillus being resistant to a histidine-antagonist.

8. The method of claim 3, wherein said recipient strain requires L-histidine for growth.

9. The method of claim 1, wherein said plasmid is pCT 127, pC 194, pC 221, pC 223, pUB 112, pUB 110, pTP 4, pTP 5, pLS 15, pLS 28, pLS 13, pPL, or pPL 2.

10. The method of claim 9, wherein said plasmid is pUB 110.

11. The method of claim 1, wherein said recipient strain is *Bacillus subtilis* AJ 11732.

12. The method of claim 1, wherein said donor strain is *Bacillus subtilis* AJ 11733.

13. The method of claim 1, wherein said L-histidine producing microorganism is *Bacillus subtilis* AJ 11734.

14. The method of claim 7, wherein said L-histidine producing microorganism is *Bacillus subtilis* AJ 11735.

* * * * *